Figure 1:
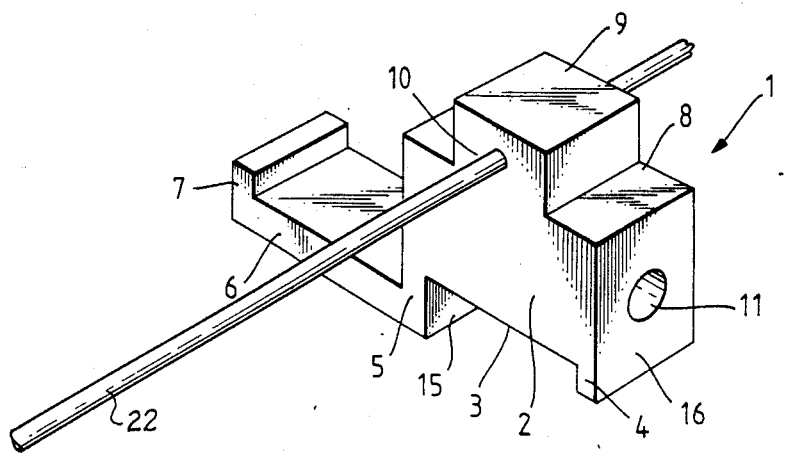

United States Patent [19]

Burrett et al.

[11] Patent Number: 4,937,049

[45] Date of Patent: Jun. 26, 1990

[54] SAMPLE TRANSFER DEVICE

[75] Inventors: Kenneth F. Burrett, Epsom Downs; James O. Molloy, Belmont, both of England; William K. Donald, Inverness, Scotland; Ian Gordon, Inverness, Scotland; Derek W. Ross, Inverness, Scotland; Alan R. Bowley, Balloch Inverness, Scotland

[73] Assignee: IBG Systems Limited, Surrey, England

[21] Appl. No.: 159,379

[22] Filed: Feb. 23, 1988

[30] Foreign Application Priority Data

Feb. 24, 1987 [GB] United Kingdom ............... 87/04267

[51] Int. Cl.$^5$ ............................................. G01N 35/00
[52] U.S. Cl. ........................................ 422/63; 422/99;
 422/100; 73/863.32
[58] Field of Search .................... 422/65, 100, 99, 63,
 422/66; 73/863.32

[56] References Cited

U.S. PATENT DOCUMENTS

| 3,269,800 | 8/1966 | Lukrec | 422/65 |
| 3,444,742 | 5/1969 | Ellis | 73/863.32 |
| 3,607,097 | 9/1971 | Auphan | 422/66 |
| 4,039,287 | 8/1977 | Moran | 422/65 |
| 4,303,611 | 12/1981 | Jessop | 422/65 |
| 4,446,104 | 5/1984 | Hammerling et al. | 422/63 |
| 4,478,094 | 10/1984 | Salomaa et al. | 73/863.32 |
| 4,528,159 | 7/1985 | Liston | 422/65 |
| 4,659,677 | 4/1987 | Glover et al. | 436/174 |
| 4,830,832 | 5/1989 | Arpagaus et al. | 422/65 |

FOREIGN PATENT DOCUMENTS 0020875 7/1981 European Pat. Off. .
2523812 9/1983 France .

Primary Examiner—Robert J. Warden
Assistant Examiner—D. John Griffith, Jr.
Attorney, Agent, or Firm—Marshall, O'Toole, Gerstein, Murray & Bicknell

[57] ABSTRACT

A transfer device including means for movement of samples from a plurality of sites of a first separation to a plurality of sites of a second, different, separation, said means comprising a plurality of sampling elements capable of movement with respect to one another between said first separation and said second separation.

The sample transfer device is particularly suited to the transfer of blood samples in blood grouping or other determinations.

A method of sample transfer is also provided.

9 Claims, 2 Drawing Sheets

U.S. Patent    Jun. 26, 1990    Sheet 1 of 2    4,937,049

SAMPLE TRANSFER DEVICE

SAMPLE TRANSFER DEVICE

This invention relates to a new sample transfer device and a new method of sample transfer.

Microplates, generally consisting of a plastics moulding containing numerous wells in a rectangular matrix, are widely used in medical laboratories as vessels in which a number of samples can be tested simultaneously.

A fundamental difficulty in designing equipment for transferring samples onto microplate wells is that the wells have a typical small spacing between centres, whilst the samples are initially presented in larger vessels which are spaced further apart because of their size. This is particularly the case with blood samples. A blood sample is collected from a donor unit in a test tube. In order to test the blood sample, it is necessary to transfer a portion of the blood sample to a microplate well. Automatic sample transfer devices are known, e.g. DE No. 3621586 and EP No. 185330, but such devices are limited to using only 1, or at most 2, sample probes. Such devices are large and cumbersome and are unable to transfer a substantially large number of samples at one time.

Surprisingly, we have now found a new sampling device which facilitates the transfer of samples from units of a given separation to units of a different separation.

According to the invention, we provide a transfer device including means for movement of samples from a plurality of sites of a first separation to a plurality of sites of a second, different, separation, said means comprising a plurality of sampling elements capable of movement with respect to one another between said first separation and said second separation.

An individual sampling element may be provided with means for moving a second, adjacent sampling element from the first separation to the second separation. The means for moving an adjacent sampling element may be for example, a cord, a chain, a hinged arm, an elastic link, an engaging arm, a spring or a piston, e.g. a lazy tongs device.

The means for moving an adjacent sampling element may act to determine the maximum separation between two adjacent sampling elements. We prefer the means for moving an adjacent sampling element to also be capable of determining maximum separation and transmitting drive to adjacent sampling elements.

The means for moving an adjacent sampling element may comprise an actuating element operably linked to an adjacent sampling element. A preferred actuating element is an extending arm provided with a terminal lip adapted to co-operate with a receptor portion, said receptor portion preferably comprises a shoulder, such that the terminal lip and the shoulder are capable of co-operation. Consequently, the length of the extending arm may determine the maximum separation between a first sampling element and a second sampling element. In addition, the extending arm may be capable of moving a second sampling element since continued motion of the first sampling element may pull the second sampling element along.

The sampling elements may be supported by the means for moving adjacent sampling elements. However, we prefer the sampling elements to be slidably mounted, e.g. upon a fixed rail. When the sampling elements are slidably mounted they may be made of any material which has low friction properties, e.g. a plastics material such as polypropylene.

The sampling elements may be placed in a linear array. The transfer device may comprise a plurality of such arrays e.g. two. The sampling elements in a first array may be provided with means for co-operating with a second array of sampling elements. The co-operating means may also act as a means for moving the adjacent array of sampling elements. The co-operating means may be, e.g. a cord, a chain, a hinged arm, an elastic link, an engaging arm or a piston. We prefer a sampling element to comprise a rib which is adapted to co-operate with one or more sampling elements of a second array.

The present invention is advantageous because it is light and portable. Furthermore, drive may be applied only to one end of one array, thus complex motors are unnecessary.

A further advantage of this sampling device is that it is capable of being operably linked to a computer. This may be particularly advantageous when handling blood samples. When donations of blood are given a sample is stored in a test tube and each tube is given a digital code, e.g. a bar code. Such labelling assists in the recordal of data allocated to any given sample. A fundamental problem with such data storage is that there is a risk that when a sample is transferred from a test tube to, for example, a microplate, any two samples may be confused and incorrect data accorded to a sample. This invention provides a method of avoiding such errors by according a second digital code to each sample. The second code may relate to a position of a sample in a given microplate. Consequently the risk of confusion may be reduced.

The present invention is particularly applicable for the transfer of fluids and especially for the transfer of liquids, e.g. blood. However, the transfer device may also be adapted for the transfer of solids. By the term blood we mean normal human or animal blood, serum, haemoglobin or any conventionally used blood products.

The invention is particularly suitable for the transfer of small volumes of fluid to a precise depositing site such as the transfer of blood samples in blood grouping or other determinations based on haemoglutination reactions. When used for transferring blood samples we prefer the sampling elements to be capable of moving from an open position in which each element is separated by a distance of 13 to 18 mm, e.g. 15 mm, from an adjacent sampling element to a closed position in which the element separation is from 6 to 12, e.g. 9 mm, and vice versa. Such transfer is particularly suited for the transfer of samples from test tubes to microplate wells.

The sampling elements may move with respect to one another in more than one plane, but we prefer the elements to move only in one plane with respect to one another, e.g. horizontal. The sampling elements may be able to move in three dimensions.

The movement of the sampling elements with respect to each other is preferably from a closed position in which the sampling elements are abutted to an open position in which the sampling elements are separated and vice versa.

The sampling elements may be biassed apart and drive means provided to cause the sampling elements to abut or, preferably, the sampling elements are biassed together and drive provided to cause separation of the sampling elements. When two arrays of sampling elements are provided drive may be applied to one or both of the arrays.

The number of sampling elements may vary according to the particular use to which the device is to be put. For use in the transfer of blood we prefer the number of sampling elements to be of from 2 to 24, preferably from 6 to 16 and most preferably from 8 to 12.

Each sampling element may carry a plurality of sample probes, however we prefer each sampling element only to carry two probes and more preferably only one probe.

The cycle of fluid transfer is faster when comparing the present invention to known sampling techniques. In particular, the cycle may be quickened by use of the fluid transfer device in conjunction with a peristaltic pump, e.g. a compressed air peristaltic pump such as that described in European Patent Application, Publication No. 0242077.

We also provide a method of simultaneously transferring a plurality of samples from a plurality of sites of a first separation to a plurality of sites of a second, different, separation which comprises simultaneously collecting a plurality of samples from the sites of the first separation, movement of the samples to the spacing of the sites of the second separation and discharging the plurality of samples into the plurality of sites of the second separation.

We further provide a method of transfer of a plurality of fluid samples as hereinbefore described, wherein a depository site is operably linked to a sample and the data is recorded on a computer.

It is a further feature of the invention to provide an individual sampling element adapted for use in a sample transfer device as hereinbefore described.

In particular we provide a sampling element comprising a supporting member and an actuating element operably linked to an adjacent sampling element. In operation an actuating element of a first sampling element moves an adjacent sampling element and also determines the maximum separation between the two sampling elements.

Figure 2:
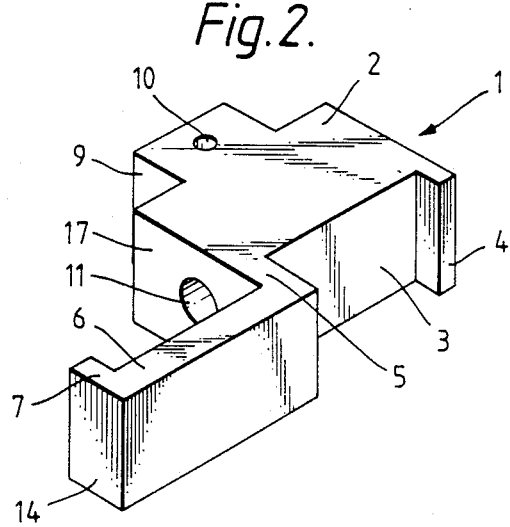
Figure 3:
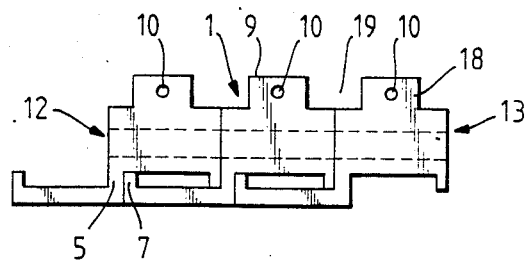
Figure 4:
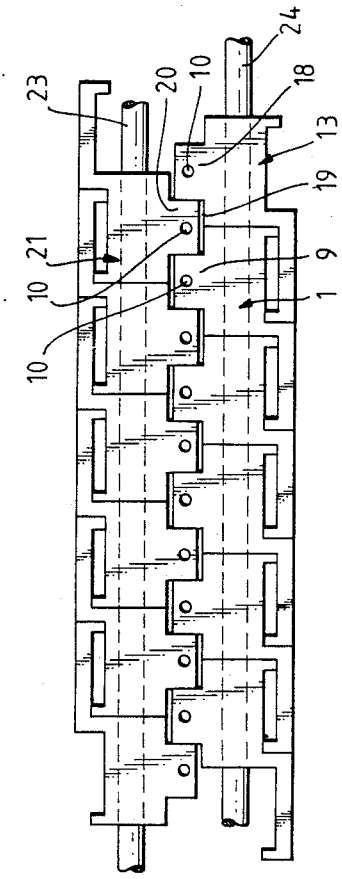
Figure 5:
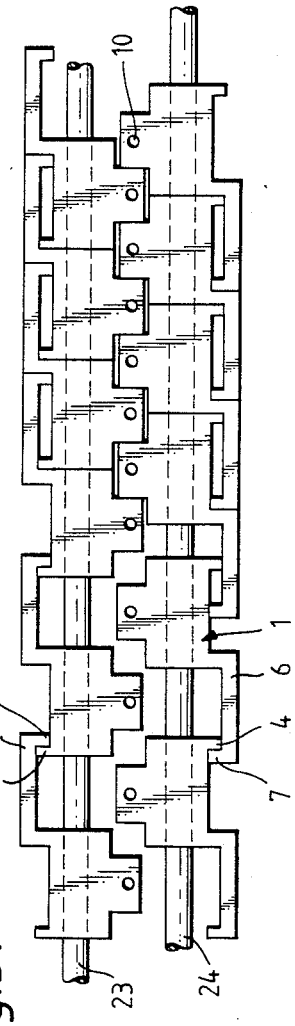
Figure 6:
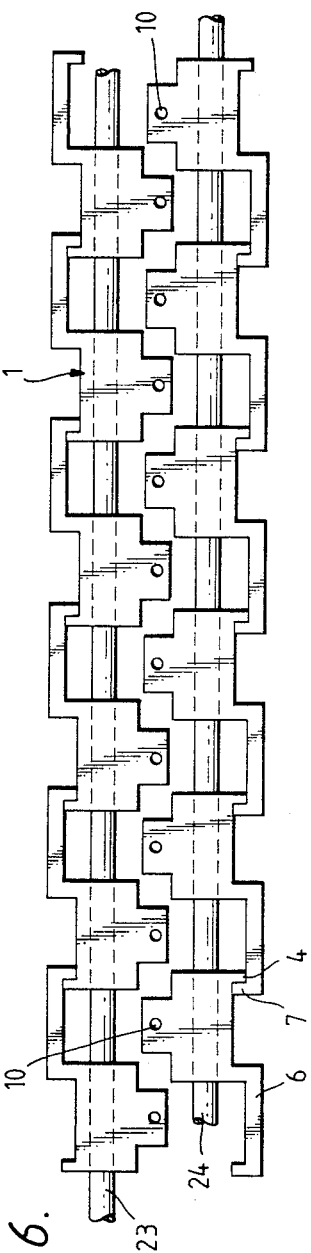

A preferred embodiment of the invention will now be described by way of example only and with reference to the accompanying drawings in which FIGS. 1 and 2 are perspective views of a single sampling element, FIG. 3 is a plan view of 3 sampling elements in an abutted position, FIG. 4 is a plan view of a series of sampling elements in the closed position, FIG. 5 is a plan view of a series of sampling elements in an intermediate position, and FIG. 6 is a plan view of a series of sampling elements in the open position.

Referring to FIGS. 1, 2 and 3, a supporting or sampling element (1) comprises a rectangular block (2) provided on a face (3) with a pair of shoulders (4 and 5), one shoulder (5) being provided with an extending arm (6) perpendicular to the shoulder (5), which arm (6) is provided with a terminal lip (7). On the face (8) opposite the shoulders (4 and 5), the block (2) is provided with an external rib (9), which rib (9) is parallel with and mid-way between the shoulders (4 and 5) and includes a longitudinal aperture (10), which carries a sampling probe 22. The body of the block (2) is also provided with an aperture (11) which is perpendicular to aperture (10).

When a sampling element (1) is abutted to two adjacent sampling elements (12 and 13), the external surface (14) of the lip (7) engages with the internal surface (15) of the shoulder (5) of the adjacent sampling element (12). In a similar fashion, the external surface (16) of the shoulder (4) engages with the external surface (17) of the shoulder (5) of the second adjacent sampling element (13).

Referring to FIGS. 3, 4 and 5. In operation two series of sampling elements are slidably mounted on two rails (23 and 24) by means of the aperture (11) such that when the sampling elements (1 and 13) of the first array are abutted, the two adjacent ribs (9 and 18) co-operate to provide a recessed portion (19) between the ribs (9 and 18). The width of the block (2) and the rib (9) is such that the recess (19) is of appropriate dimensions to locate the rib (20) of a facing sampling element (21) or a second array. The width of the block (2) and the rib (9) determine the separation of two adjacent apertures (10) when the sampling elements (1) are in the closed position.

Drive is applied to the two outermost sampling elements at one end of each array and the two outermost sampling elements are moved away from a first separation relative to the other sampling elements to a second separation. When the maximum separation is reached, the shoulder (4) engages with the lip (7) of the arm (6) of an adjacent sampling element and the drive is transmitted to that sampling element.

The drive continues until all of the sampling elements are at their maximum separation as determined by the length of the arm (6).

A sample may be taken from an array of sites of a first separation. The arrays of sampling elements may then be driven to a second separation and moved to a depositing site. The samples may then be deposited at an array of sites of a second separation.

We claim:

1. A transfer device for moving samples between a plurality of sites of a first separation and a plurality of sites of a second, different, separation, said device comprising a linear guide member, a plurality of supporting elements mounted along said linear guide member to form a linear array of supporting elements, and sampling probe supporting means for supporting at least one sampling probe provided on each said supporting element, wherein said supporting elements are positionable along said linear guide member in a first position in which said supporting elements are generally in abutment and said sampling probe supporting means have a first, minimum separation, and in a second position in which said supporting elements are spaced apart and said sampling probe supporting means have a second, maximum separation, and wherein each said supporting element carries an actuating element which cooperates with an adjacent supporting element, each said actuating element being arranged to determine the spacing between two adjacent supporting elements when said supporting elements are in their second position and thereby to determine said maximum separation of said sampling probe supporting means.

2. A transfer device according to claim 1, further comprising a shoulder formed on each said supporting element with which the actuating element of an adjacent supporting element engages, wherein each said actuating element comprises an arm attached to a respective one of said supporting elements and a lip carried by said arm, and wherein each said arm extends away from its respective supporting element such that in said second, spaced apart position of said supporting elements, the shoulder of each supporting element is engaged by the lip of the actuating element of an adjacent supporting element whereby the arm of said adjacent supporting element determines said maximum separation of said sampling probe supporting means.

3. A transfer device according to claim 1, wherein said supporting elements are substantially indentical, and wherein each said supporting element comprises a member having first and second, spaced, opposed external surfaces, the first external surface of said supporting element being generally in abutment with the second external surface of an adjacent supporting element when said supporting elements are in their first position.

4. A transfer device according to claim 3, wherein at least one aperture extends through said member of each supporting element from the first external surface to the second external surface thereof, and wherein said linear guide member comprises at least one elongate guide rail which is arranged to extend through said one aperture of each said supporting element whereby said supporting elements are mounted along said guide rail to form said linear array, and such that said supporting elements are slidable along said guide rail.

5. A transfer device according to claim 1, comprising a plurality of arrays of supporting elements, wherein each said array is linear and is provided with means arranged to cooperate with an adjacent array of supporting elements.

6. A transfer device according to claim 1, wherein the transfer device is operably linked to a computer such that data related to a sample in a sampling probe at a first site may be related to the same sample when moved to a second site.

7. A transfer device for moving samples between a plurality of sites of a first separation and a plurality of sites of a second, different, separation, said device comprising a linear guide member, a plurality of supporting elements mounted along said linear guide member to form a linear array of supporting elements, and a plurality of sampling probes, each said sampling probe being carried by a respective one of said supporting elements, wherein said supporting elements are positionable along said linear guide member in a first position in which said supporting elements are generally in abutment and said sampling probes have a first, minimum separation, and in a second position in which said supporting elements are spaced apart and said sampling probes have a second, maximum separation, wherein said supporting elements are substantially identical and each carries an actuating element in the form of an arm carrying a lip, and wherein each said supporting element has a shoulder formed thereon with which the lip of the actuating element of an adjacent supporting element is arranged to engage, each said lip being arranged to engage said respective shoulder when said supporting elements are in their second position whereby the arms of said actuating elements determine said maximum separation of said sampling probes.

8. A transfer device according to claim 7, further comprising at least one aperture extending through each said supporting element, and wherein said linear guide member comprises at least one elongate guide rail which is arranged to extend through said one aperture of each said supporting element whereby said supporting elements are mounted along said guide rail to form said linear array, and such that said supporting elements are slidable along said guide rail.

9. A transfer device according to claim 8, further comprising means for moving at least one said supporting element along said guide rail, and wherein said actuating elements are arranged such that movement of one supporting element away from an adjacent supporting element causes engagement between the shoulder and lip of the adjacent supporting element and thereby moves the adjacent supporting element.

* * * * *